United States Patent [19]
Barriere et al.

[11] Patent Number: 5,948,755
[45] Date of Patent: Sep. 7, 1999

[54] CYCLOSPORIN COMPOUND, ITS PREPARATION AND THE PHARMACEUTICAL COMPOSITIONS WHICH CONTAIN IT

[75] Inventors: Jean-Claude Barriere, Bures Sur Yvette; Georges Bashiardes, Thiais; Jean-Christophe Carry, Meudon; Michel Evers, La Queue En Brie; Bruno Filoche, Creteil; Serge Mignani, Chatenay-Malabry, all of France

[73] Assignee: Rhone-Poulenc Rorer S.A., France

[21] Appl. No.: 08/997,613

[22] Filed: Dec. 23, 1997

[30] Foreign Application Priority Data

Dec. 24, 1996 [FR] France .................................. 96 15954

[51] Int. Cl.$^6$ .............................. A61K 37/02; C07K 7/64
[52] U.S. Cl. ................................ 514/11; 514/9; 530/317; 530/321
[58] Field of Search .................... 530/317, 321; 514/9, 11

[56] References Cited

U.S. PATENT DOCUMENTS

| | | | |
|---|---|---|---|
| 4,703,033 | 10/1987 | Seebach | 514/11 |
| 4,771,122 | 9/1988 | Seebach | 530/317 |
| 4,814,323 | 3/1989 | Andrieu et al. | 514/11 |

FOREIGN PATENT DOCUMENTS

| | | |
|---|---|---|
| A-0484281 | 5/1992 | European Pat. Off. |
| 95111162 | 7/1995 | European Pat. Off. |
| WO 97/04005 | 2/1997 | WIPO |

OTHER PUBLICATIONS

Papageorgiou et al., "Anti HIV–1 Activity of a Hydrophilic Cyclosporin Derivative With Improved Binding Affinity to Cyclophilin A," Bioorganic & Medicinal Chemistry Letters, 6(1):23–26 (1996).

Mikol et al., "The Role of Water Molecules in the Structure-Based Design of (5–Hydroxynorvaline)–2–cyclosporin: Synthesis, Biological Activity, and Crystallographic Analysis With Cyclophilin A," J. Med. Chem., 38(17):3361–3367 (1995).

Billich et al., "Mode of Action of SDZ NIM 811, a Non-immunosuppressive Cyclosporin A Analog with Activity Against Human Immunodeficiency Virus (HIV) Type 1: Interference with HIV Protein Cyclophilin A Interactions," J. of Virology, 69(4):2451–2461, (1995).

*Primary Examiner*—Cecilia J. Tsang
*Attorney, Agent, or Firm*—Finnegan, Henderson, Farabow, Garrett & Dunner, L.L.P.

[57] ABSTRACT

The cyclosporin compound of formula (I) is particularly useful in the treatment and/or prophylaxis of retrovirus infections.

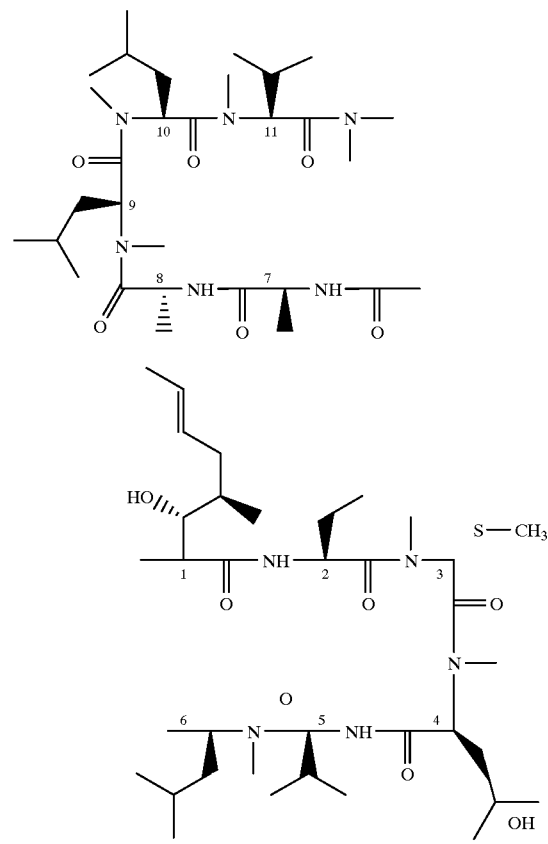

6 Claims, No Drawings

CYCLOSPORIN COMPOUND, ITS PREPARATION AND THE PHARMACEUTICAL COMPOSITIONS WHICH CONTAIN IT

The technology involved in this application is related to that disclosed in the following co-pending U.S. applications, filed on even date herewith:

(1) Title: Novel Cyclosporin Compounds, Their Preparation and the Pharmaceutical Compositions Which Contain Them Inventors: Jean-Claude Barriere, Georges Bashiardes, Jean-Christophe Carry, Michel Evers, Bruno Filoche, and Serge Mignani Attorney Docket No.: 03806.0420 U.S. patent application Ser. No. 08/997,612, Filed Dec. 23, 1997.

(2) Title: Cyclosporin Compounds, Their Preparation and the Pharmaceutical Compositions Which Contain Them Inventors: Jean-Claude Barriere, Georges Bashiardes, Jean-Christophe Carry, Michel Evers, Bruno Filoche, Jean-Pierre Leconte, and Serge Mignani Attorney Docket No.: 03806.0421 U.S. patent application Ser. No. 08/996,699, Filed Dec. 23, 1997.

The specifications of these related applications are hereby specifically incorporated by reference.

The present invention relates to a cyclosporin compound of formula (I):

to its preparation and to the pharmaceutical compositions which contain it.

The inventive compound is useful in the treatment and/or prophylaxis of retrovirus infections, and more particularly of AIDS (acquired immunodeficiency syndrome) and of associated syndromes [ARC (AIDS related complex)]. The inventive derivative exhibits the advantage of being very weakly immunosuppressing.

Cyclosporin compounds modified at the 3-position have been previously described as immunosuppressants, in European Patent EP 194,972.

Variously modified cyclosporin compounds, in particular the compound [4'-hydroxy-MeLeul]$^4$-cyclosporin, have been described previously in European Patent EP 484281 and in Eur. J. Immunol., 17, 1359 (1987). These compounds are useful in the treatment of AIDS and are not immunosuppressants.

A description has been given, in Bioorganic and Medicinal Chemistry Letters, 6(1), 23–26 (1996), of the cyclosporin compound of formula:

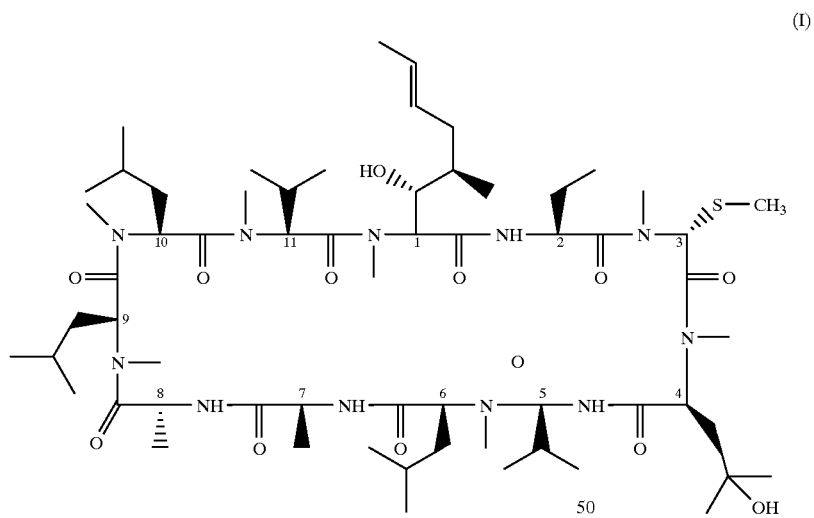

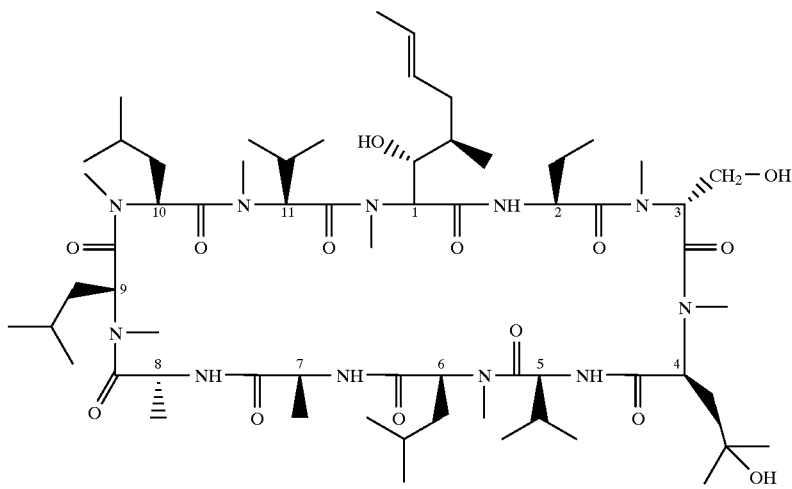

which possesses anti-HIV-1 activity.

It has now been found that the cyclosporin compound of formula (I) is particularly advantageous due to its powerful activity and its very weak immunosuppressing nature.

According to the present invention, the product of formula (I) can be obtained by reaction of dimethyl disulphide with an activated form of a [4'-hydroxy-MeLeu]$^4$-cyclosporin derivative of formula (II):

(II)

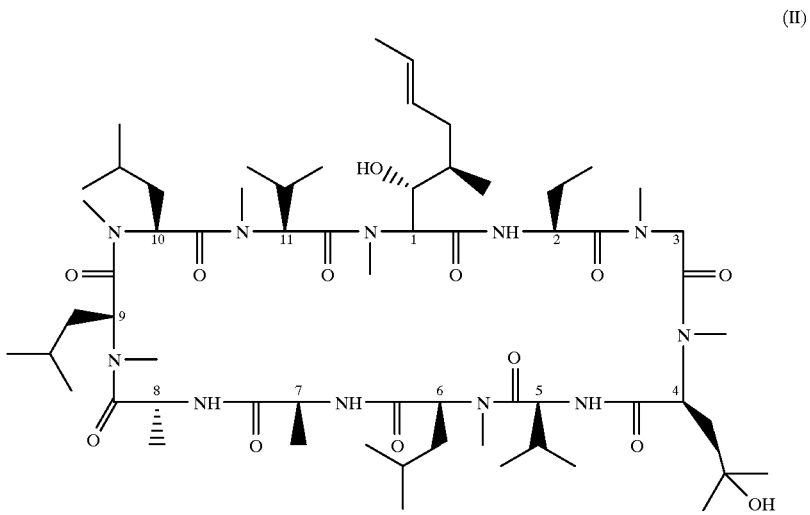

The activated form of the cyclosporin of formula (II) is understood to mean a form activated on the sarcosine at the 3-position. This activated form is preferably prepared in situ. Activation is generally carried out under an inert atmosphere, by treatment with an organometallic derivative, in particular a lithium derivative, such as n-butyllithium, lithium diisopropylamide or a mixture, for example.

The addition of dimethyl disulphide is advantageously carried out in an organic solvent, such as a hydrocarbon, for example, hexane, or an ether, for example, diethyl ether, tetrahydrofuran or t-butyl methyl ether, at a temperature of between −78 and 0° C. The operation is preferably carried out under nitrogen.

The [4'-hydroxy-MeLeu]$^4$-cyclosporin derivative of formula (II) can be prepared as described in European Patent Application EP 484,281, the disclosure of which is incorporated herein by reference.

The novel cyclosporin compound of formula (I) can be purified, if appropriate, by physical methods, such as crystallization or chromatography.

The novel cyclosporin compound according to the present invention is particularly useful in the prophylaxis and treatment of retrovirus diseases and more particularly of AIDS and of associated syndromes. Prophylaxis is understood to mean in particular the treatment of subjects who have been exposed to HIV viruses, in particular asymptomatic seropositives who present the risk of developing the disease in the months or years to come after the primary infection.

The product according to the invention displays an anti-retrovirus activity at concentrations devoid of any cytotoxic or cytostatic effect.

The activity of the product of formula (I) has been demonstrated in the techniques described by Pauwells et al., J. Virol. Meth., 20, 309 (1988) and by O. Schwatz et al., AIDS Research and Human Retroviruses, 4(6), 441–48 (1988) and cited by J. F. Mayaux et al., Proc. Nat. Acad. Sci. USA, 91, 3564–68 (1994). In these techniques, the average for the active concentrations is 70 or 50 nM (IC$_{50}$), the disclosure of each of which is incorporated herein by reference.

The following example illustrates the present invention.

EXAMPLE

[(R)-Methylthio-Sar]$^3$-[4'-hydroxy-MeLeu]$^4$-cyclosporin A was prepared according to the following method:

111 cm$^3$ of a 1.6M solution of n-butyllithium in hexane were added over 20 minutes to a solution, cooled to a temperature in the region of −10° C. and under nitrogen, of 25.2 cm$^3$ of diisopropylamine (distilled beforehand over calcium hydride) in 330 cm$^3$ of tetrahydrofuran (distilled beforehand over sodium), the temperature being maintained at 0° C. The mixture was stirred at 0° C. for 20 minutes and was then cooled to a temperature in the region of −78° C. The solution thus obtained was transferred under nitrogen, via a transfer tube, onto a solution of 14.45 g of [4'hydroxy-MeLeu]$^4$-cyclosporin A in 290 cm$^3$ of tetrahydrofuran cooled beforehand to a temperature in the region of −78° C., the temperature being maintained at approximately −68° C. The resulting mixture was stirred at a temperature in the region of −76° C. for 20 minutes and then 52 cm$^3$ of a 1.6M solution of n-butyllithium in hexane were added over 10 minutes. Stirring was maintained for 30 minutes and then 22 cm$^3$ of dimethyl disulphide were added over 10 minutes, the temperature being maintained at approximately −75° C. The mixture was stirred at a temperature in the region of −78° C. for 2 hours and then at 0° C. for 18 hours. A mixture of 300 cm$^3$ of distilled water and 37 cm$^3$ of 36% aqueous hydrochloric acid was poured slowly onto the reaction mixture, the mixture was then separated by settling and the aqueous phase was washed with 200 cm$^3$ of diethyl ether. The organic extracts were combined, washed with 100 cm$^3$ of saturated sodium chloride solution, dried over sodium sulphate, filtered and concentrated under reduced pressure (2.7 kPa) at a temperature in the region of 40° C.

The solid obtained was triturated in 200 cm$^3$ of pentane, filtered, washed with pentane and then purified by flash chromatography on a silica column (0.04–0.063 mm), elution being carried out with a gradient (0 to 15% acetone/100–85% ethyl acetate, per volume of 500 cm$^3$ by 1-cm$^3$ steps) and 35-cm$^3$ fractions were collected. The fractions containing the expected product were combined and concentrated under reduced pressure (2.7 kPa) at a temperature in the region of 40° C. to give a solid which was triturated in 20 cm$^3$ of pentane. After filtration, 2 g of [(R)-methylthio-Sar]$^3$-[4'-hydroxy-MeLeu]$^4$-cyclosporin A were obtained in the form of a white solid melting at approximately 140° C.

$^1$H N.M.R. spectrum (400 MHz, CDCl$_3$, δ in ppm): 1.27 (d, J=7 Hz, 3H, 8β CH$_3$), 1.37 (d, J=7.5 Hz, 3H, 7β CH$_3$), 1.64 (d, J=5 Hz, 3H, CH$_3$ at 1γ), from 1.65 to 1.80 and 2.41 (respectively mt and dd, J=15 and 6.5 Hz, each 1H, 4β CH$_2$), 2.17 (s, 3H, SCH$_3$), 2.47 (mt, 1H, 5β CH), 2.71, 3.13, 3.18, 3.27, 3.46 and 3.52 (6 s, respectively 6H, 3H, 3H, 3H, 3H and 3H, 7 NCH$_3$), 3.70 (d, J=6.5 Hz, 1H, OH at 1β), 3.78 (mt, 1H, 1β CH), 4.56 (mt, 1H, 7α CH), 4.67 (t, J=9 Hz, 1H, 5α CH), 4.86 (mt, 1H, 8α CH), 5.00 (dd, J=9 and 6 Hz, 1H, α CH of a leucine), from 5.05 to 5.15 (mt, 2H, 2α CH and α CH of a leucine), 5.15 (d, J=11 Hz, 1H, 11α CH), from 5.25 to 5.40 (mt, 2H, CH=CH), 5.45 (t, J=6.5 Hz, 1H, 4α CH), 5.52 (d, J=6 Hz, 1H, 1α CH), 5.72 (dd, J=10.5 and 4Hz, 1H, α CH of a leucine), 5.75 (s, 1H, 3α CH), 7.16 (d, J=8 Hz, 1H, CONH at 8), 7.52 (d, J=9 Hz, 1H, CONH at 5), 7.65 (d, J=7.5 Hz, 1H, CONH at 7), 7.94 (d, J=9.5 Hz, 1H, CONH at 2).

[4'-Hydroxy-MeLeu]$^4$-cyclosporin A was prepared according to the method described in Patent EP 484,281, the disclosure of which is specifically incorporated by reference herein.

The present invention also relates to pharmaceutical compositions containing the product of formula (I), if appropriate in the salt form, either alone or in the form of a combination with one or more compatible and pharmaceutically acceptable diluents or adjuvants or with another anti-retrovirus agent, optionally intended for the treatment of AIDS, or an antiviral, immunomodulating or antimicrobial agent.

The composition according to the invention is capable of keeping alive cells infected with a retrovirus, such as, for example, the HIV, and thus of reducing progression towards AIDS or of decreasing its seriousness in subjects already infected by reducing the mortality of infected cells. The compositions can be used orally, parenterally, rectally or in aerosols.

The pharmaceutical compositions can be used curatively or preventively in subjects exhibiting immunodeficiency and/or infected by a retrovirus. Of course, the makeup of these compositions will be suited to the specific case of the digestive system of the immunodepressed subjects.

Use may be made, as solid compositions for oral administration, of tablets, pills, hard gelatin capsules, powders or granules. In these compositions, the active product according to the invention is mixed with one or more inert diluents or adjuvants, such as sucrose, lactose or starch.

These compositions can comprise substances other than diluents, for example a lubricant, such as magnesium stearate, or a coating intended for controlled release.

Use may be made, as liquid compositions for oral administration, of solutions which are pharmaceutically acceptable, suspensions, emulsions, syrups and elixirs containing inert diluents, such as water or liquid paraffin. These compositions can also comprise substances other than diluents, for example wetting, sweetening or flavoring products.

The compositions for parenteral administration can be emulsions or sterile solutions. Use may be made, as solvent or vehicle, of propylene glycol, a polyethylene glycol, vegetable oils, in particular olive oil, or injectable organic esters, for example ethyl oleate.

These compositions can also contain adjuvants, in particular wetting, isotonizing, emulsifying, dispersing and stabilizing agents.

Sterilization can be carried out in several ways, for example using a bacteriological filter, by radiation or by heating. They can also be prepared in the form of sterile solid compositions which can be dissolved at the time of use in sterile water or any other injectable sterile medium.

The compositions for rectal administration are suppositories or rectal capsules which contain, in addition to the active principle, excipients such as cocoa butter, semisynthetic glycerides or polyethylene glycols.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle with a particle size of 30 to 80 λ.m, for example dextran, mannitol or lactose.

In human therapeutics, the doctor will determine the posology which he considers most appropriate according to a preventive or curative treatment and according to the age, weight, stage of the infection and other factors specific to the subject to be treated. Generally, doses are between 5 and 30 mg/kg by the oral route for an adult.

In addition, it has been shown that the cyclosporin compound of formula (I) displays a synergistic effect when it is combined with other antiviral agents which are active with respect to retroviruses. The present invention also relates to synergistic combinations which contain the cyclosporin compound of formula (I) and an active principle known for its activity with respect to retroviruses.

The agents known for their activity with respect to retroviruses which can be combined are chosen from agents which are compatible and inert with respect to the cyclosporin derivative of formula (I), both in the category of pharmacological treatments and in the category of alternative treatments, such as gene and cell or antisense therapy. Without implied limitation, these agents constituting the various therapeutic classes are chosen, for example, from nucleoside reverse transcriptase inhibitors (NRTI) and non-nucleoside reverse transcriptase inhibitors (NNRTI) [zidovudine (AZT), didanosine (DDI), dideoxycytidine (DDC), d4T, ribavirin, 3TC, nevirapin, and the like], from protease inhibitors [such as, for example, Saquinavir, Ritonavir, Indinavir and Nelfinavir], integrase inhibitors [such as AR177], from therapy gene inhibitors targeting the regulatory proteins of HIV replication, such as inhibitors of the rev protein [such as, for example, Rev M10], or nucleocapsid inhibitors [such as, for example, DIBAs], from inhibitors targeting the specific messenger RNA transcripts of all the HIVs, such as, for example, the antisense ones [such as GEM92, GPI-2A and the like], from inhibitors of the family of modulators of cellular dNTP [such as hydroxyurea], from cytokine inhibitors [such as TNF], from inhibitors of entry of HIVs [such as T20, SPC-3, and the like], and from agents constituting therapeutic classes used in vaccinal approaches, both by biotechnology [such as HIVAC-1e, ALVAC, and the like] and by compounds acting with respect to the immune response [such as RG-8394].

The cyclosporin compound according to the invention in particular displays a particularly advantageous synergistic effect when it is combined with AZT, ddI and/or Saquinavir.

The pharmaceutical compositions comprising such combinations, optionally in the presence of pharmaceutically acceptable excipients, are also within the scope of the present invention.

The following example illustrates a composition according to the invention.

Formulation Example

A formulation was prepared which was administered by the oral route and which had the following composition:

| | |
|---|---|
| [(R)-Methylthio-Sar]³-[4'-hydroxy-MeLeu]⁴-cyclosporin A | 250 mg |
| Magnesium stearate | 3 mg |
| Acidsol | 15 mg |
| Colloidal silica | 2 mg |
| Lactose | 130 mg |

What is claimed is:

1. A cyclosporin compound of the formula (I):

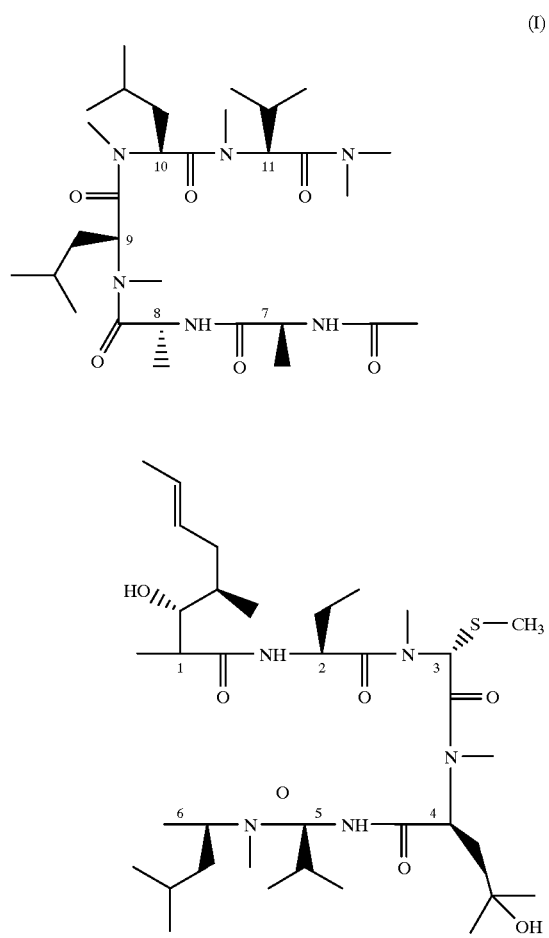

2. A process for preparing a cyclosporin compound of formula (I) according to claim 1, said process comprising reacting dimethyl disulphide with an activated form of a [4'hydroxy-MeLeu]⁴-cyclosporin compound of the formula (II):

(II)

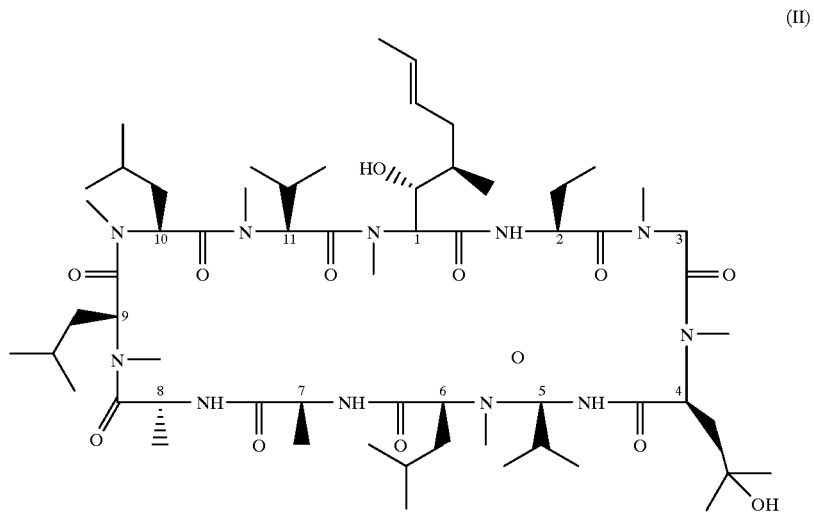

under conditions sufficient to obtain a compound of formula (I).

3. A pharmaceutical composition, comprising a cyclosporin compound of formula (I) according to claim 1, said cyclosporin compound being present alone or in combination with any compatible and pharmaceutically acceptable carrier.

4. A pharmaceutical composition according to claim 3, said composition further comprising at least one antiviral, immunomodulating or antimicrobial active agent.

5. A synergistic composition comprising a cyclosporin compound of formula (I) according to claim 1 and further comprising at least one anti-retroviral agent.

6. A synergistic composition according to claim 5, wherein said anti-retroviral agent is AZT, ddI or Saquinavir.

* * * * *